(12) United States Patent
Moffitt et al.

(10) Patent No.: US 10,231,865 B2
(45) Date of Patent: Mar. 19, 2019

(54) ENDOCAVITY TEMPERATURE CONTROL DEVICE

(71) Applicant: Profound Medical Inc., Toronto (CA)

(72) Inventors: Owen Moffitt, Toronto (CA); Michael Wybenga, Toronto (CA)

(73) Assignee: Profound Medical Inc., Mississauga, ON (CA)

( * ) Notice: Subject to any disclaimer, the term of this patent is extended or adjusted under 35 U.S.C. 154(b) by 312 days.

(21) Appl. No.: 14/988,056

(22) Filed: Jan. 5, 2016

(65) Prior Publication Data

US 2016/0193076 A1 Jul. 7, 2016

Related U.S. Application Data

(60) Provisional application No. 62/099,873, filed on Jan. 5, 2015.

(51) Int. Cl.
| | | |
|---|---|---|
| A61F 7/00 | (2006.01) | |
| A61F 7/12 | (2006.01) | |
| A61N 7/00 | (2006.01) | |

(52) U.S. Cl.
CPC ........ *A61F 7/12* (2013.01); *A61F 2007/0028* (2013.01); *A61F 2007/0054* (2013.01); *A61F 2007/0091* (2013.01); *A61N 7/00* (2013.01)

(58) Field of Classification Search
CPC .............. A61F 2007/0056; A61F 7/123; A61F 2007/0028; A61F 2007/0091
See application file for complete search history.

(56) References Cited

U.S. PATENT DOCUMENTS

| | | | |
|---|---|---|---|
| 787,920 A | | 4/1905 | Hofman |
| 4,841,970 A | * | 6/1989 | Rand .......................... A61F 7/12 606/21 |
| 4,844,073 A | * | 7/1989 | Pohler ....................... A61F 7/12 607/113 |
| 5,474,071 A | | 12/1995 | Chapelon et al. |
| 5,649,973 A | | 7/1997 | Tierney et al. |
| 5,733,316 A | * | 3/1998 | Tierney .................. A61B 18/18 607/101 |
| 5,792,070 A | * | 8/1998 | Kauphusman ........... A61B 5/01 600/549 |

(Continued)

FOREIGN PATENT DOCUMENTS

WO WO2012005996 1/2012

OTHER PUBLICATIONS

Canadian Intellectual Property Office, "International Search Report and the Written Opinion of the International Searching Authority", dated Jul. 14, 2016, WIPO.

(Continued)

*Primary Examiner* — Kaitlyn E Smith
(74) *Attorney, Agent, or Firm* — Intrinsic Law Corp.

(57) ABSTRACT

An apparatus for temperature controlling an endocavity such as the rectum during thermal therapy of nearby tissues is disclosed. In some aspects the apparatus is mechanically configured to best conform to the patient. In other aspects the apparatus is designed to eliminate gas bubbles from forming or accumulating in certain volumes that would interfere with the thermal therapy. In other aspects the apparatus is optimized for use in cooling the rectum during ultrasound thermal therapy of the prostate.

31 Claims, 9 Drawing Sheets

(56) References Cited

U.S. PATENT DOCUMENTS

| | | | |
|---|---|---|---|
| 6,009,351 A * | 12/1999 | Flachman | A61B 18/1815 607/101 |
| 6,071,238 A * | 6/2000 | Chapelon | A61B 8/12 600/439 |
| 6,159,207 A | 12/2000 | Yoon | |
| 6,224,590 B1 * | 5/2001 | Daikuzono | A61N 5/0601 606/10 |
| 6,348,039 B1 | 2/2002 | Flachman et al. | |
| 6,726,708 B2 * | 4/2004 | Lasheras | A61F 7/123 606/21 |
| 7,387,638 B2 | 6/2008 | Gonzales | |
| 7,491,223 B2 * | 2/2009 | Lasheras | A61F 7/123 606/21 |
| 8,414,501 B2 * | 4/2013 | Hanley | A61B 5/4381 374/158 |
| 2002/0004675 A1 * | 1/2002 | Lasheras | A61F 7/123 607/105 |
| 2002/0010502 A1 * | 1/2002 | Trachtenberg | A61F 7/123 607/102 |
| 2002/0116041 A1 | 8/2002 | Daoud | |
| 2003/0144593 A1 | 7/2003 | Whitmore et al. | |
| 2004/0024434 A1 | 2/2004 | Yang et al. | |
| 2004/0199229 A1 * | 10/2004 | Lasheras | A61F 7/123 607/105 |
| 2007/0167775 A1 * | 7/2007 | Kochavi | A61B 5/6885 600/439 |
| 2007/0239062 A1 * | 10/2007 | Chopra | A61B 5/01 600/549 |
| 2008/0215042 A1 | 9/2008 | Swanson | |
| 2008/0275306 A1 * | 11/2008 | Rebuffat | A61B 1/31 600/184 |
| 2009/0018446 A1 * | 1/2009 | Medan | A61N 7/022 600/439 |
| 2009/0157070 A1 | 6/2009 | Oskin et al. | |
| 2009/0171238 A1 * | 7/2009 | Hanley | A61B 5/01 600/549 |
| 2009/0270955 A1 * | 10/2009 | Magers | A61B 5/01 607/105 |
| 2011/0319748 A1 * | 12/2011 | Bronskill | A61B 18/00 600/420 |
| 2012/0323296 A1 * | 12/2012 | Takeda | A61F 7/10 607/105 |
| 2014/0200568 A1 * | 7/2014 | Sharma | A61B 18/04 606/27 |
| 2015/0297139 A1 * | 10/2015 | Toth | A61B 18/18 600/381 |
| 2016/0082180 A1 * | 3/2016 | Toth | A61M 5/142 600/1 |
| 2017/0065343 A1 * | 3/2017 | Mickelsen | A61B 18/1492 |
| 2017/0143403 A1 * | 5/2017 | Nau, Jr. | A61B 18/082 |

OTHER PUBLICATIONS

EPO as ISA, "Extended European Search Report", PCT/IB2016/000439, dated Sep. 11, 2017.

* cited by examiner

ENDOCAVITY TEMPERATURE CONTROL DEVICE

RELATED APPLICATIONS

This application claims the benefit of and priority to U.S. Provisional Application No. 62/099,873, entitled "Endocavity Temperature Control Device," filed on Jan. 5, 2015, which is incorporated herein by reference.

TECHNICAL FIELD

The present application generally relates to devices for controlling the temperature of a body cavity and surrounding tissue, and more particularly, to devices for controlling said temperature in the context of a thermal therapy applied to an organ or tissues that are proximal to said cavity.

BACKGROUND

Several methods for treating diseased tissues using thermal therapy are in use. Thermal therapy involves application of thermal energy (heat) to a diseased region or organ. The proper application of heat can eliminate or reduce the disease by killing diseased cells in the organ. Cancer cells can be treated by the application of a proper amount of heat or by heating to a certain temperature. Thermal therapy has been applied to the treatment of prostate cancer, but other diseased organs and tissues may similarly be treated. The modality for applying the thermal treatment may vary, and the art teaches the use of RF electromagnetic energy, laser and ultrasound energy for heating a target region. Some prostate thermal treatments are externally delivered by an energy delivery device outside the general volume of the prostate or even outside of the body of the patient, e.g., focused ultrasound surgery. Other prostate thermal treatments are internally delivered from within the general volume of the prostate, e.g., using transurethral energy sources delivering energy from within the urethra outwardly into the surrounding volume of the prostate.

FIG. 1 illustrates a general arrangement of a male patient in cross section 10. Existing thermal therapy treatment procedures can vary, but in a class of treatments the patient may lie supine as shown and the prostate 100 is subjected to thermal heating from a therapy applicator source, which can be a laser, RF antenna, ultrasound transducer or other source. The prostate 100 generally surrounds the urethra. Therefore, a class of treatments inserts a narrow applicator (not shown) into the urethra 120 of the patient and guides the active portion of the applicator until it is substantially surrounded by the prostate 100. This type of treatment is called transurethral because it delivers energy into the prostate 100 from within the urethra 120.

An unwanted side effect of the heating of the diseased tissue can be the over-heating of adjacent non-diseased tissue and organs. This is because the heating effects of the thermal therapy procedure have a finite spatial distribution that makes it difficult or impossible to fully heat the target zone while not heating the surrounding volumes at all. Also, the living body causes heat conduction and perfusion to spread the thermal therapy heat to volumes in the vicinity of the intended target volume. Specifically, as an example, in the thermal therapy of the prostate, the rectum 110 and other healthy tissues near the prostate 100 can be heated beyond what is safe or healthy for the patient. It is desired to limit the thermal dose or maximum temperature applied to these tissues, e.g., to the rectum wall 112 proximal to the prostate 120. The term "proximal" is used herein as commonly used in patent specifications to denote things that are adjacent to or near one another.

Some existing protocols employ cooling methods and devices to keep the temperature rise in healthy tissues around the target volume to within a safe limit. These protocols, e.g., US Pub. No. 2011/0319748 A1, disclose a heat exchange apparatus that is placed into a body cavity (e.g., the rectum through orifice 130) and that receives a temperature-controlled cooling fluid (e.g., water) to cool the rectum during the thermal therapy of the prostate 100. The present application is directed to a mechanically and thermally optimized cooling device for cooling the rectum 110 and its walls 112 during thermal therapy procedures in its vicinity, including during thermal therapy to the prostate 100.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

In an aspect, the invention is directed to an endocavity thermal control device. The device includes an elongated body having an insertable portion for insertion into a rectum of a patient and an external portion that remains external to the rectum, wherein the insertable portion includes a distal portion and a proximal portion disposed at with respect to one another, the body angle from 100 to 150 degrees. The body angle may be obtuse (i.e., greater than 90 degrees but less than 180 degrees).

The device also includes a fluid circuit in the body that substantially extends from the external portion to the insertable portion, the fluid circuit configured to circulate a thermal fluid into and out of the insertable portion. The device also includes a thermal window disposed on a surface of the insertable portion, the thermal window configured to be positioned adjacent to a prostate when the device is inserted into the rectum, the thermal window in thermal communication with the thermal fluid.

In another aspect, the invention is directed to a method of controlling a temperature of a prostate during thermal therapy of a patient. The method includes inserting an endocavity thermal control device into a rectal cavity of the patient, the device comprising an elongated body having an insertable portion and an external portion, wherein the insertable portion includes a distal portion and a proximal portion disposed at a body angle with respect to one another, the body angle from 100 to 150 degrees. The method also includes positioning the body to conform to a notch in a rectal wall adjacent to an apex of the prostate, the notch formed when a thermal therapy device is inserted into a urethra of the patient. The method also includes inflating a balloon disposed on the body of the device. The method also includes pressing the balloon against a first rectal wall distal to the prostate to cause a thermal window on the body to contact a second rectal wall proximal to the prostate. The method also includes circulating a thermal fluid in a fluid circuit in the body, the fluid circuit extending from an external portion to an internal portion of the body, the thermal fluid in thermal communication with the thermal window.

IN THE DRAWINGS

For a fuller understanding of the nature and advantages of the present invention, reference is be made to the following detailed description of preferred embodiments and in connection with the accompanying drawings, in which.

DETAILED DESCRIPTION

Thermal therapy procedures can benefit from spatially designed cooling to tissues and organs that are not diseased but that lie near the thermal therapy target zone. In the case of thermal therapy of the prostate, as an example, it is helpful to cool the rectum and rectal walls near the prostate to avoid over-heating these tissues. The apparatus described below will provide a much-needed controllable and configurable cooling profile within a patient's rectum for use with prostate thermal therapy and in some aspects with ultrasound thermal therapy of the prostate.

It is to be understood that the present disclosure is often illustrated in the context of an endocavity being the rectum, but the present invention is not so limited, and can be applied to other cavities as would be appreciated by those skilled in the art with suitable modifications to the size and form factor of the device, without departing from the spirit of the invention. It is also to be understood that the present disclosure can be applied to cooling as well as to heating. For example, the device can be used to remove thermal energy or lower the temperature of a cavity and surrounding tissue, but can be used to add thermal energy or raise the temperature of a cavity and surrounding tissue as needed and depending on the medical procedure at hand.

Figure 1:
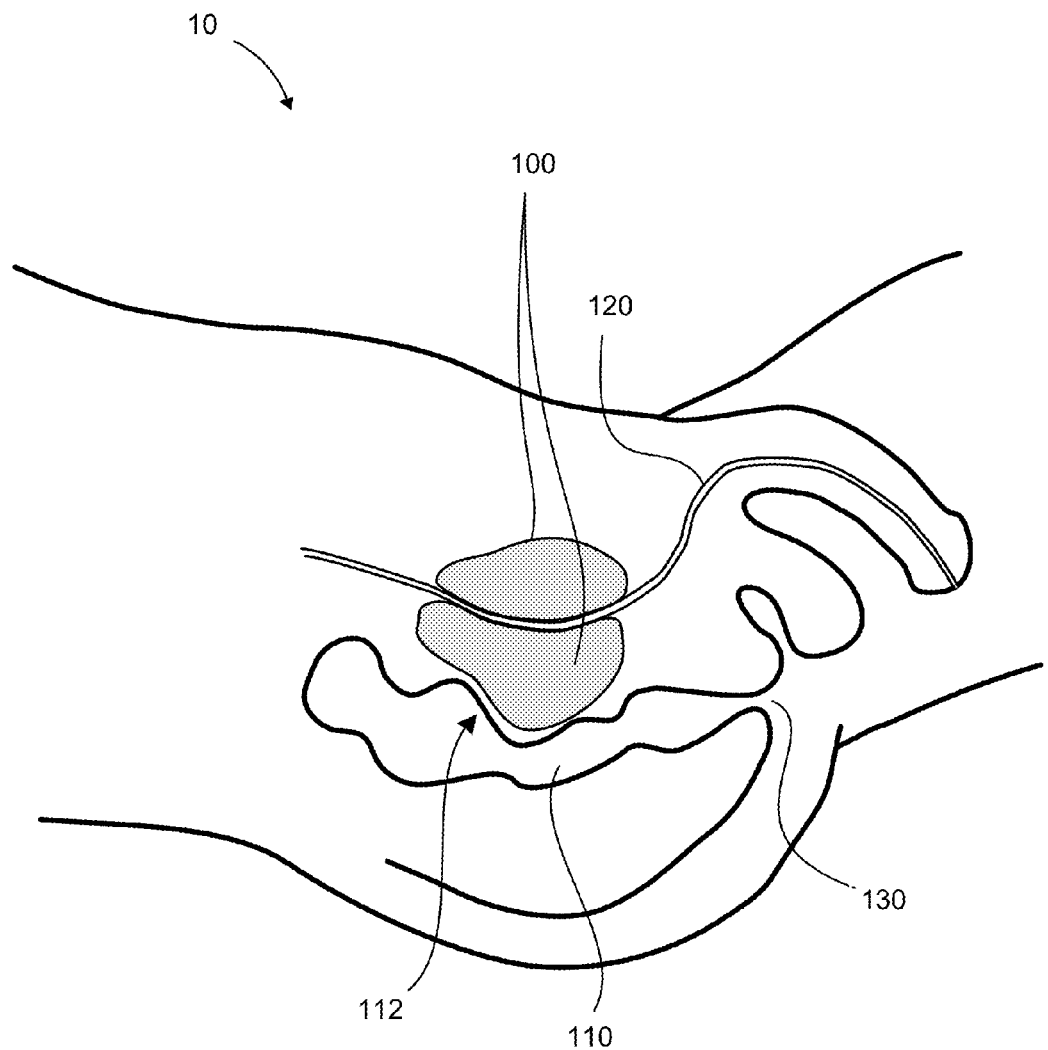
FIG. 1 illustrates a cross sectional view of a male patient according to the prior art.
Figure 2:
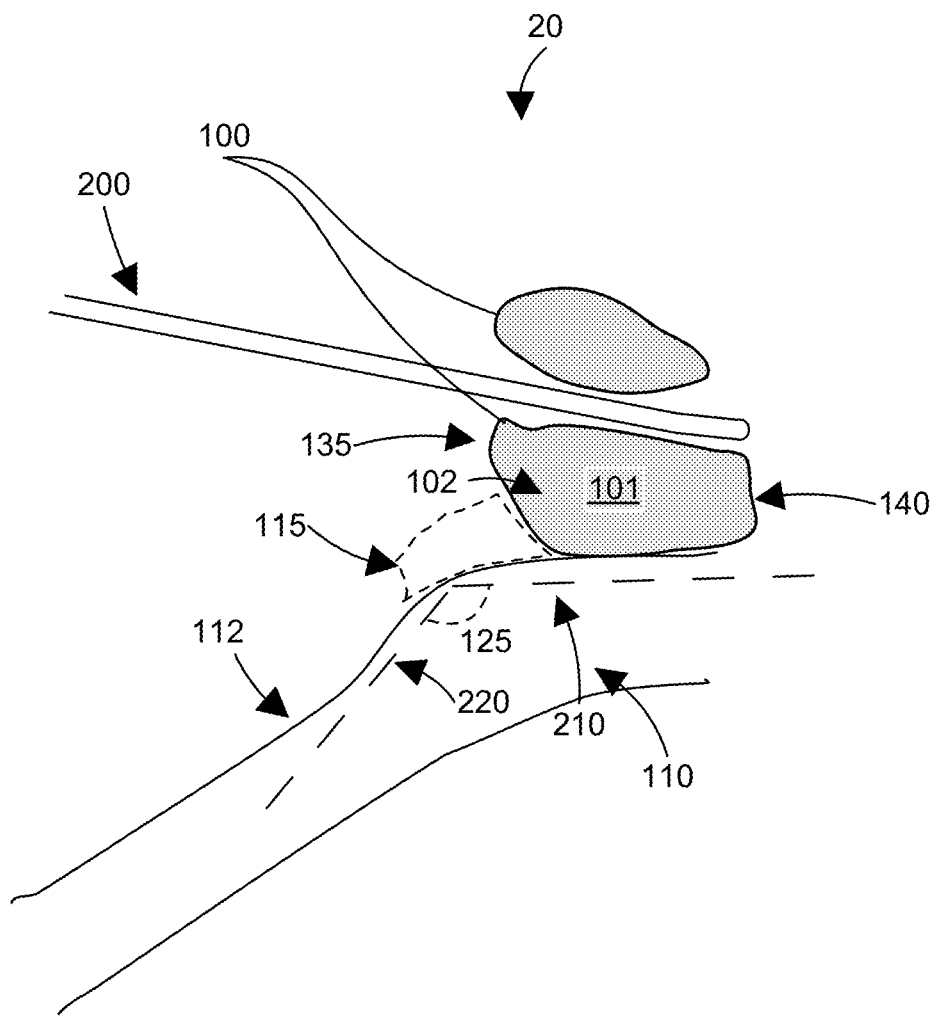
FIG. 2 illustrates a portion of a male patient undergoing thermal therapy treatment.

FIG. 2 illustrates a portion 20 of a male patient undergoing thermal therapy treatment. An applicator 200 is inserted through the male urethra (not illustrated) until it is adjacent to the prostate 100. As discussed above, the applicator 200 can include a laser, an RF antenna, an ultrasound transducer or other heat source. The inserted applicator 200 applies pressure to the lower portion 101 of the prostate 100. The pressure causes a displacement 102 of the lower portion 101 of the prostate 100. The displacement 102 is generally towards the applicator 200 and away from the rectum 110. The displacement 102 can cause a gap or notch 115 (illustrated by dotted lines) along the rectum wall 112 adjacent to the displacement 102 of the prostate 100. The displacement 102 of the prostate 100 occurs proximal to an apex 135 of the prostate 100. The notch 115 has a notch angle 125 which can be defined by lines parallel to the rectum wall 112 proximal and distal to the notch 115. Base 140 and apex 135 are on opposing sides of the prostate 100.

In general, the notch angle 125 is between a first line 210 that is generally parallel to the rectum wall 112 proximal to the notch 115 and a second line 220 that is generally parallel to the rectum wall distal to the notch 115. The notch angle can be about 75 degrees to about 175 degrees, about 100 degrees to about 150 degrees, about 115 to about 130 degrees, about 125 degrees, or any value between any of the above ranges. As used herein, "about" means plus or minus 10% of the relevant value. In addition, the notch 115 has a radius of about 5 to about 20 mm, about 10 to about 15 mm, about 12 mm, or any value between any of the above ranges. It is to be appreciated that the particular examples and embodiments appearing herein are exemplary and for the purpose of illustration only. Those skilled in the art will understand that the present methods and devices can be applied in other particular embodiments depending on the circumstance at hand.

Figure 3:
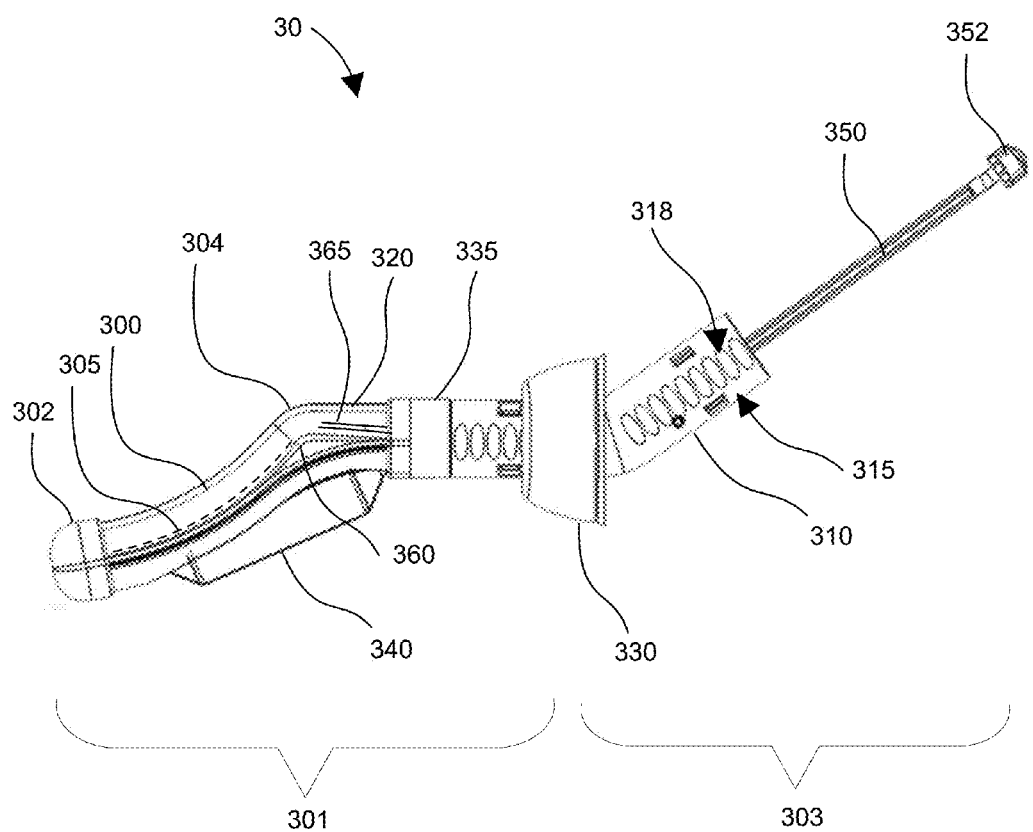
FIG. 3 illustrates a side view of an endocavity thermal control device 30 according to an embodiment.

FIG. 3 illustrates a side view of an endocavity thermal control device 30 according to an embodiment. The device shown is designed and configured for cooling of the rectum and rectal wall and nearby tissue in the context of a prostate thermal therapy procedure. However, the principles illustrated by this embodiment can be extended by those skilled in the art for application to other procedures and body cavities. In an embodiment, the device 30 is configured to conform to the rectum of a male patient including a rectal notch caused by the insertion of a thermal therapy probe, as discussed above.

The device 30 comprises a body with a frame or shell or housing 300 that may include one or several parts joined together so as to be substantially rigid in their overall frame. The housing 300 can be formed out of one or more biocompatible materials. For example, the housing 300 can be formed out of one or more biocompatible rigid plastics such as acrylonitrile butadiene styrene (commonly referred to as ABS). In addition or in the alternative, the housing 300 can be formed out of one or more biocompatible metals, such as stainless steel or titanium, and/or one or more biocompatible ceramics, such as aluminum oxide, zirconia, or calcium phospates. The device can be considered as having a first insertable or internal portion 301 that is inserted into a patient's body (e.g., in the rectal cavity) during a procedure and a second portion 303 that remains outside of the patient's body. A flange or collar 330 can be positioned to define or limit which portions of the device 30 enter the patient's body and which portions remain outside of the patient's body during use. Collar 330 can be moveable in some embodiments to allow for custom sizing and positioning of the collar to define the extent of insertable portion 301. In the alternative, the second portion 303 can have a flared shape or an expanding diameter (e.g., a conical shape) to prevent over-insertion in which case collar 330 is not needed.

The shell or housing 300 can also be defined by two opposing ends thereof. One end 302 having a forward tip that is inserted into the patient's endocavity in advance of the following portions of insertable portion 301; the other end 352 comprising a terminator or connector that can be coupled to other electrical and/or mechanical ports or terminals. Fluid flow plenums are disposed near the tip of end 302 for circulating thermal fluid into and then back out of the device 30.

A handle 310 comprises a grip 315 allowing convenient holding of the device 30 by an operator who can apply torque or force to the device to insert, retract or rotate the device 30 within a patient's body. Collar 330 also assists in securing the device 30 from inadvertent over-insertion or unwanted movement and can help secure the operator's hand to the handle 310 while using the device 30. In addition, the collar 330 can shield the operator's hand from contacting the patient's skin proximal to the endocavity (e.g., to prevent contamination). The collar 330 can be moved to discrete positions at notches or raised ribs 318 along the grip 315 to vary the maximum depth of insertion of device 30 in the endocavity. The notches/raised ribs 318 can mate with complementary features (raised ribs or notches) of the collar 330 to mechanically secure the collar 330 at a given location.

Electrical and/or fluid conduits 360 pass through a shaft 350 so that they are terminated in suitable connection points at terminus 352. For example, electrical sensor wires may pass in and out of the body 300 of the device 30 to deliver temperature measurements measured by temperature sensors (e.g., thermocouples) disposed at one or more locations in the device 30 or on the external surface of the device 30. Other actuators and sensors may also be incorporated into the device as needed.

The fluid conduits 360 can carry a thermal control fluid into and out of the device 30 to control the temperature of a patient's endocavity. The fluid and electrical conduits 360 within the device 30 are described further below, and can extend to and from the ends 302, 352 of the device 30 and to points in between.

A thermal exchange (e.g., heating or cooling) window 320 is formed into one face of the housing 300, which is the primary place heat is exchanged between the thermal control fluid inside the device and the patient's body surrounding the device. The window 320 can be constructed out a material that (a) has a high thermal conductivity so as to transfer heat from the tissue to the thermal control fluid, (b) has a high mechanical strength to be durable, (c) is rigid to maintain its shape under pressure, (d) has a similar acoustic impedance to the thermal control fluid to minimize reflection of incident ultrasound energy, (e) has a similar magnetic susceptibility to the thermal control fluid to minimize the introduction of magnetic susceptibility artifacts, (f) is biocompatible, and (g) is MRI compatible. For example, the window 320 can be formed of titanium, aluminum, or polyethylene. In a specific embodiment, the window 320 includes polyethylene and/or a polyethylene terephthalate having a thickness of about 0.001 inches to about 0.003 inches or about 0.002 inches The window 320 can have a longer extent than the extent of the nearby prostate organ so that axial placement of the device 30 is not an overly sensitive operation (leaving some room for error in the axial placement of the device 20). In some embodiments, the window 320 extends from a bend 304 in the housing 300 to the front tip 302. In some embodiments, the widow extends from a neck 335 to the front tip 302, the neck 335 disposed between the bend 304 and the collar 330. The neck 335 can be about 15 to about 45 mm or about 30 mm axially from the bend 304. Again, the particular examples above are provided to illustrate the nature of the invention, and those skilled in the art may devise equivalent, similar or alternative aspects equally comprehended by this disclosure.

A variable volume fluid-fillable balloon or bladder 340 is disposed on a side of the housing 300, typically opposing the side of the window 320 and/or the bend 304. The operator can control a fluid (e.g., with a manual or automated syringe) to inflate or deflate the balloon or bladder 340. The balloon or bladder 340 can be filled with a fluid such as air, water, oil, saline, gel, or an aqueous solution, that can cause balloon or bladder 340 to increase or decrease in volume and cross sectional girth. When expanded, the balloon or bladder 340 pushes against the walls of the endocavity, which in turn causes the entire device 30 including the thermal exchange window 320 to be pressed against the walls of the endocavity proximal to the window 320. The balloon 340 can be operated by the operator using a control setting on the handle 310 of the device 30 or remotely by way of a driving signal applied to a pressure actuator, pump, or other mechanism for forcing fluid (gas, liquid) into or out of the balloon 340 to control its size. In some embodiments, the operator connects a syringe to the device 30 (e.g., at a port in terminus 352) to fill the balloon 340. The syringe controlled manually or automatically to force fluid into or out of the balloon 340. In a non-limiting example, the balloon 340 can be inflated to about 10 mm to about 20 mm, 20 mm to about 30 mm, about 15 mm, about 25 mm, or an value therebetween, in diameter outwardly from the body 300 of device 30.

Housing 300 may be manufactured in a number of sizes and geometries. In one example, the housing 300 has a length and general diameter suited to the medical procedure and endocavity it is being used with. Housing 300 can include bent, curved or contoured features as shown to adapt the device 30 for rectal cooling applications according to the general size and shape of an expected endorectal cavity. A bend 304 defines a general change in the axial direction of the housing 300 of device 30. In some embodiments, the bend 304 is configured to align with a position and/or angle of the notch 115 on the rectal wall 112, as discussed above. For example, the bend 304 can have a bend angle of 75 degrees to about 175 degrees, about 100 degrees to about 150 degrees, about 115 to about 130 degrees, about 125 degrees, or any value between any of the above angles. Once again, the present disclosure illustrates the invention by way of particular examples, which are not intended to be exhaustive or exclusive of the applications and embodiments possible under the invention.

The device 30 can also have a curved contour in some portions to fit more securely and closely around an anatomy of interest. For example, the insertable portion 301 can include a curve 305 that extends from the bend 304 to the forward end 302. The curve 305 is generally upward or concave so that the forward end 302 is angled towards the bend 304 and away from the patient's spine (not illustrated). The curve 305 can be defined as an arc of a circle having a given radius. An increase in the radius decreases the curvature of curve 305. In some embodiments, the device 30 has a straight or a substantially straight contour (i.e., a "curve" defined by a "circle" having an infinite radius). In some embodiments, the curve 305 is defined by a circle having a radius of about 50 mm to about 200 mm, about 75 mm to about 175 mm, about 100 mm to about 150 mm, about 125 mm, or any range between any of the above values. In a particular embodiment, the curve 305 is defined by a circle having a radius of about 110 mm. In some embodiments, the curve 305 is defined by a circle having a radius of greater than 200 mm. Plastics and injection molded polymers and cast materials can be used to make a rigid or substantially rigid housing 300 of the desired shape and size for an application at hand.

It has been observed by the present inventors that gas pockets or bubbles may tend to accumulate locally near certain parts of an endocavity. In rectal cooling applications, gas can collect at interfaces between the device 30 and the rectal wall, e.g., in the notch discussed above. The shape of the exemplary device 30 including the bend 304 can minimize or prevent such gas bubbles from forming. Furthermore, inflating expandable balloon 340 causes the upper side of device 30 to press against the rectal walls between device 30 and the prostate, moving unwanted gas bubbles away from that interface. Such gas bubbles can cause reflection of ultrasound energy, which can cause unwanted heating of the endocavity tissue proximal to the reflection. In addition, the air bubbles can cause MRI imaging artifacts that make it difficult to position the device 30 and/or to view the surrounding tissue. Further, the air bubbles are insulating and thus reduce the effectiveness of the thermal controls of device 30.

Air may initially fill the fluid conduits 360 running through the thermal control device 30, especially if the device 30 is being used for the first time, after it has been in storage, or if the device is inserted into the patient outside of the treatment/imaging chamber. In some cases, it is more economical and efficient for the practitioner or treatment facility to spend the time inserting the device into the patient in a separate room prior to taking the patient into the treatment room, e.g., a MRI imaging chamber. Here, any air or gas that was in the thermal fluid tubes 360 of the device is first purged from the device 30 prior to use so that only a desired cooling fluid (e.g., sterilized water or saline solution) is present in the fluid circuit of the device during use. For example, this gas purging step can take place once the patient is brought into the treatment/imaging chamber. In the present embodiment, it is desired to avoid air pockets in the device 30 near the thermal exchange window 320 also because such inclusions could inhibit the thermal interaction between the device 30 and the adjacent tissue being controlled. In addition, air pockets/bubbles can cause MRI imaging artifacts that make it difficult to position the device 30 and/or to view the surrounding tissue. If the device 30 is used for cooling, the presence of gas bubbles or a layer of unwanted gas having poor thermal conductivity along the interior of thermal exchange window 320 would degrade the performance of the device 30. The air bubbles can also cause ultrasound reflection, as discussed above. Accordingly, purge jet 365 allows for removal of such unwanted gas pockets and bubbles from the vicinity of the thermal exchange window 320. The purge jet 365 is disposed at the top of housing 300 in the insertable portion 301 of device 30. In an aspect, the fluid purge jet 365 provides a turbulent high velocity fluid stream (e.g., water) to dislodge trapped bubbles from the vicinity of said thermal exchange window 320.

In an aspect, the thermal fluid of the device 30 may be water, e.g., sterilized water. In a further aspect, the fluid may be water mixed with an appropriate surfactant to reduce surface tension of said water and/or to match the hydrophobicity of the water to that of the device's thermal exchange window 320. This will allow small air bubbles to detach from the window 320 and to coalesce elsewhere, or to be washed away by the flow of water. In a non-limiting example, the surfactant may comprise Span 80 (sorbitan monooleate) and/or Tween 80 (polysorbate 80), or similar substances. The thermal fluid can also include manganese chloride ($MnCl_2$) to reduce and/or eliminate MRI imaging artifacts due to fluid flow.

Figure 4:
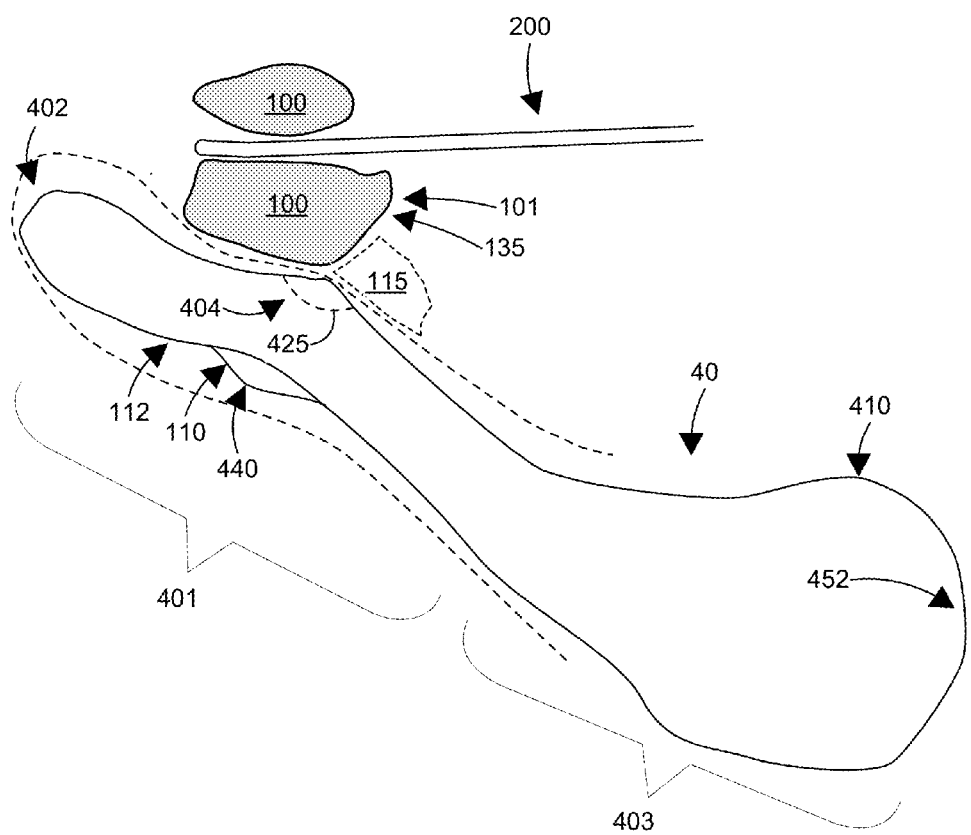
FIG. 4 is a side view of endocavity thermal control device inserted into a male rectum according to an embodiment.

FIG. 4 is a side view of an endocavity thermal control device 40 inserted into a male rectum 110 according to an embodiment. The device 40 includes an insertable portion 401 and a second portion 403. The insertable portion 401 includes a bend 404 that aligns with the notch 115 proximal to the lower portion 101 of prostate 100. As discussed above, the notch 115 is located proximal to the apex 135 of the prostate. The bend 404 and the notch 115 can have the same or different angles 425, 125, respectively, and can have any of the angles discussed above. Notch angle 125 is not illustrated in FIG. 4 for clarity. In some embodiments, the bend angle 425 and the notch angle 125 are each about 135 degrees. A balloon 440 can inflate below the bend 404 and can press against the wall 112 of the rectum 110, which can cause the device 40 including its cooling window (not illustrated), to contact the wall 112 adjacent to the prostate 100. The device 40 can lower or maintain the temperature of the prostate 100 during thermal treatment with probe 200.

The second portion 403 of the device 40 has a flared or bulbous handle 410 that increases in width or radius from the middle of the device 40 to the end 452. The increasing width of the handle 410 can prevent over insertion of the device 40 into a patient (e.g., into the rectum 110 of a patient). In addition or in the alternative, the increasing width of handle 410 can prevent or reduce movement of the device 40 after it has been inserted into the endocavity. The flared/bulbous handle 410 can also enhance control of the rotational orientation/alignment of the device 40 in the endocavity. For example, an operator rotating a handle having a relatively large diameter can move its circumference further for a given degree of rotation than a handle having a relatively smaller diameter.

Figure 5:
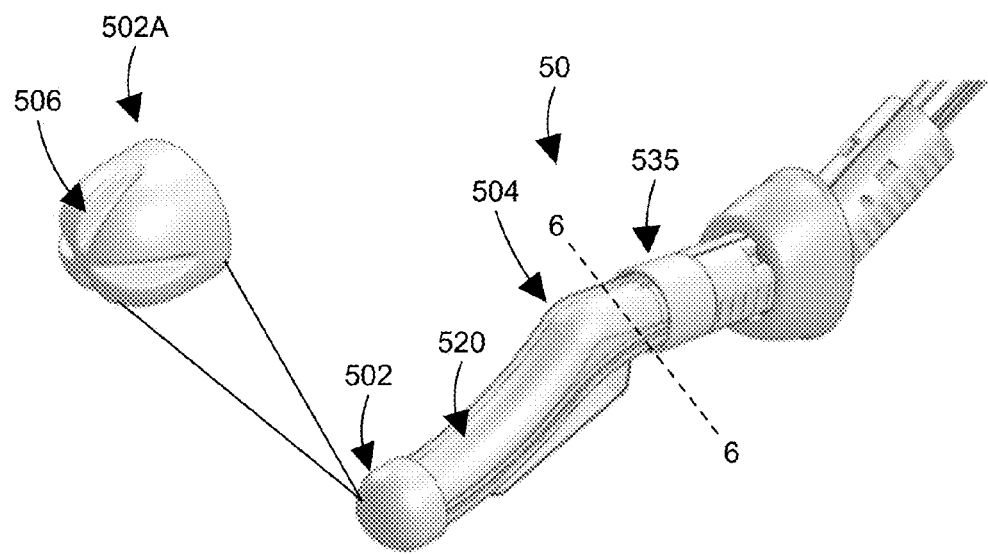
FIG. 5 is a perspective view of an endocavity thermal control device according to an embodiment.

FIG. 5 is a perspective view of an endocavity thermal control device 50 according to an embodiment. The device 50 includes a thermal exchange window 520 that may extend from the tip 502 to the neck 535. Since the thermal exchange window 520 is disposed on either side of the bend 504, the device 50 can provide adequate thermal regulation for a patient without having to be placed precisely in the relevant endocavity. For example, the device 50 can still provide heating or cooling to the prostate even if the bend 504 is not aligned with the notch in the rectal wall. In addition, in some patients the prostate extends on both sides of the notch. In order for the device 50 to provide adequate cooling for such patients, the thermal exchange window 520 can also extend across the notch so it is adjacent the prostate on both sides of the notch.

FIG. 5 also illustrates that the tip 502 can have flutes or channels 506 for example as illustrated in tip 502A. The flutes 506 can provide venting of air trapped at the tip 502, 502A when the device 50 is inserted into the endocavity. Thus, the flutes 506 can prevent or reduce the introduction of air into the endocavity on insertion of the device 50, which can prevent or reduce air bubbles caused by insertion of the device 50. The tip 502A has four flutes 506 but in some embodiments there are additional or fewer flutes 506. For example, the tip 502A can have 3 to 8 flutes 506, or any value therebetween such as 6 flutes. Each flute 506 can have a width of about 1 mm to 2 mm or about 1.5 mm, and a depth of about 0.5 mm to about 1.5 mm or about 0.75 mm. In some embodiments, the flutes 506 have a variable or non-uniform width and/or depth.

A lubricant can be used on the exterior of the device 50 to enhance patient comfort and to minimize bubble formation, for example as the device 50 is inserted into the endocavity. The lubricant can be water based, transparent to ultrasound and MRI, and bacteriostatic. The lubricant should have a low enough viscosity so as to not occlude the flutes 506, and not to trap new bubbles as the lubricant is applied to the device. Since gas (e.g., air) can scatter or reflect energy waves in the surrounding tissues, the presence of gas bubbles or pockets or voids is generally to be avoided during ultrasound or other thermal therapies. In the case of ultrasound thermal therapy, unwanted gas pockets and bubbles interacting with the applied ultrasound field can cause undesired heating of tissues in the vicinity of the bubbles or other unintended consequences of the field-bubble interaction. In some embodiments, the lubricant can be a urological gel. In particular embodiments, the lubricant can be ENDOSGEL® (FARCO-PHARMA GmbH) or MUKO® (Cardinal Health Canada Inc.).

Figure 6:
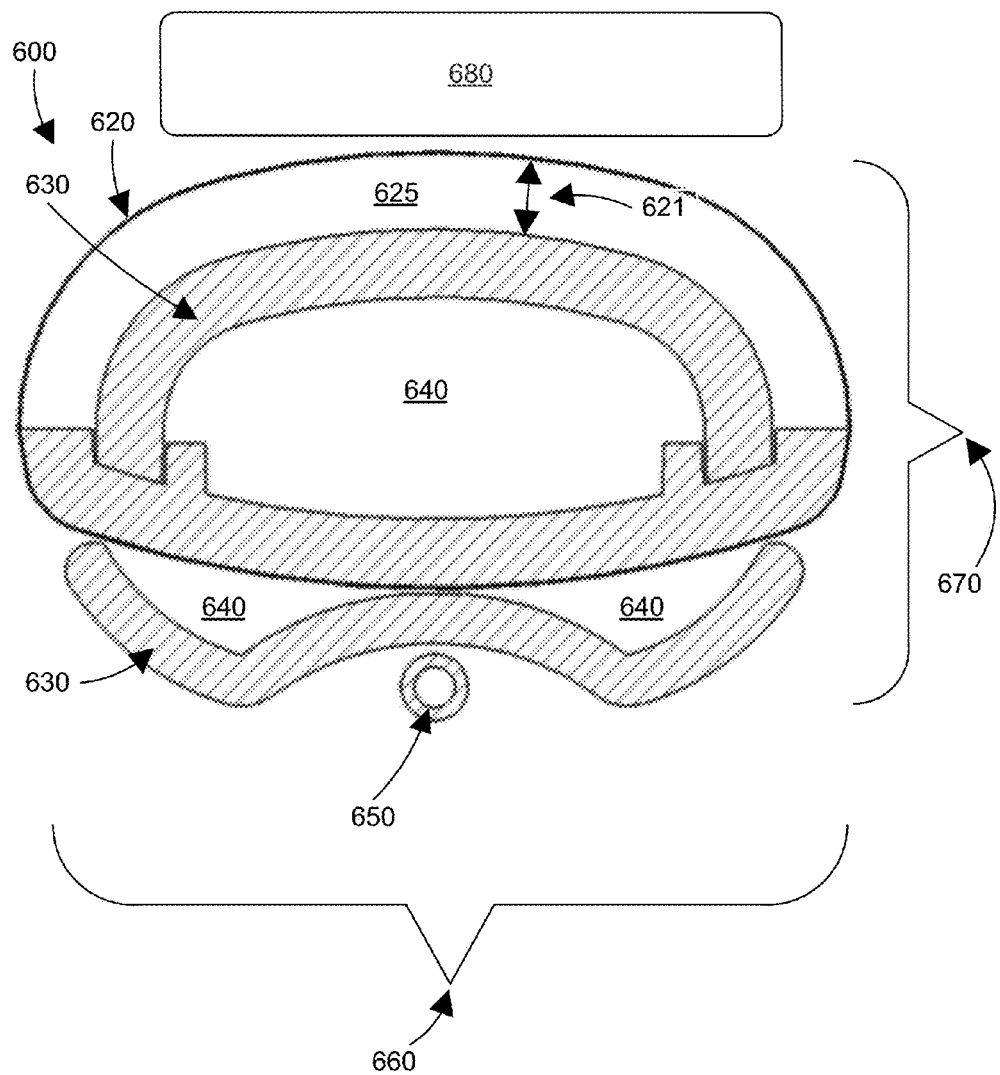
FIG. 6 is a cross section of a representative portion of an insertable portion of an endocavity thermal control device.

FIG. 6 is a cross section 600 of a representative portion (through line 6-6) of the insertable portion of the device. The cross section 600 includes a thermal exchange window 620, an inner housing 630, and fluid egress channels 640. A fluid cavity 625 is defined between the thermal exchange window 620 and the inner housing 630. The inner housing 630 can include a biocompatible rigid plastic, such as ABS. The fluid cavity 625 can have a thickness 621 of about 1.25 mm to about 2.5 mm including about 1.5 mm, about 1.75 mm, about 2.0 mm, about 2.25 mm, or any value between any of these numbers. The thickness 621 can be uniform or variable along the length of the window 620. In some embodiments, the window 620 has a thickness 621 of about 2.25 mm at or proximal to the bend and a thickness 621' (not illustrated) of about 1.5 mm at or proximal to the tip, with a tapered thickness therebetween. The foregoing examples, like the other examples described herein, are provided for the sake of illustration and not intended to limit the scope of the invention.

As illustrated in FIG. 6, the cross section 600 is generally oval in shape. The oval shape has a width 660 and a height 670. The width 660 is selected to be large enough to cover the tissue or organ 680 (e.g., prostate) to be temperature controlled during therapy. In some embodiments, the width 660 is about 15 mm to about 30 mm including about 18 mm, about 20 mm, about 22 mm, about 24 mm, about 26 mm, about 28 mm, or any width between any two of the foregoing widths. The height 670 can be about. The window 620 extends along the perimeter of the oval to form a horseshoe shape or an upside down "U" shape. As such, the window 620 extends along at least a portion (e.g., half) of the height 670 of the oval. This allows the device to be positioned in the endocavity with some rotational error. For example, the device can be rotated about 10 degrees to about 20 degrees or about 15 degrees off center from the organ 680 and the window 620 will still be positioned adjacent the organ 680 to provide temperature control thereto. The rotational error also prevents the inner housing 630 from being exposed to (e.g., in line of sight of) the ultrasound elements in the applicator, which would undesirably cause the housing 630 to heat up. Although the cross section 600 is illustrated as oval, other cross sectional shapes can be used consistent with this disclosure.

In operation, a fluid (e.g., water) is pumped into the device from the handle (e.g., through a fluid port) through the fluid cavity 625 to the tip of the device. The fluid fills a fluid plenum and then follows a return path through the fluid egress channels 640.

A pump or vacuum can be applied to the fluid egress channels 640, to circulate the fluid. The fluid can pass through an external heat exchanger to heat or cool the fluid as desired. Temperature feedback can be used to control the heat exchanger, such as the temperature of the prostate measured using MRI. The circulating fluid causes the thermal exchange window 620 to increase or decrease in temperature depending on the relative temperature of the fluid. Likewise, the thermal exchange window 620 conducts thermal energy to or from body fluids or tissue in contact with the window 620, such as the internal walls of the rectal cavity. Contact between the window 620 and the internal walls can be improved with one or more inflatable balloons, as discussed above. The cooled or warmed walls of the rectal cavity (or other endocavity) can cause the prostate to be cooled or warmed, which can maintain the temperature of the prostate during a thermal therapy procedure. A temperature of the prostate can be measured during therapy (e.g., through MRI) and the temperature of the thermal fluid can be adjusted accordingly.

Figure 7:
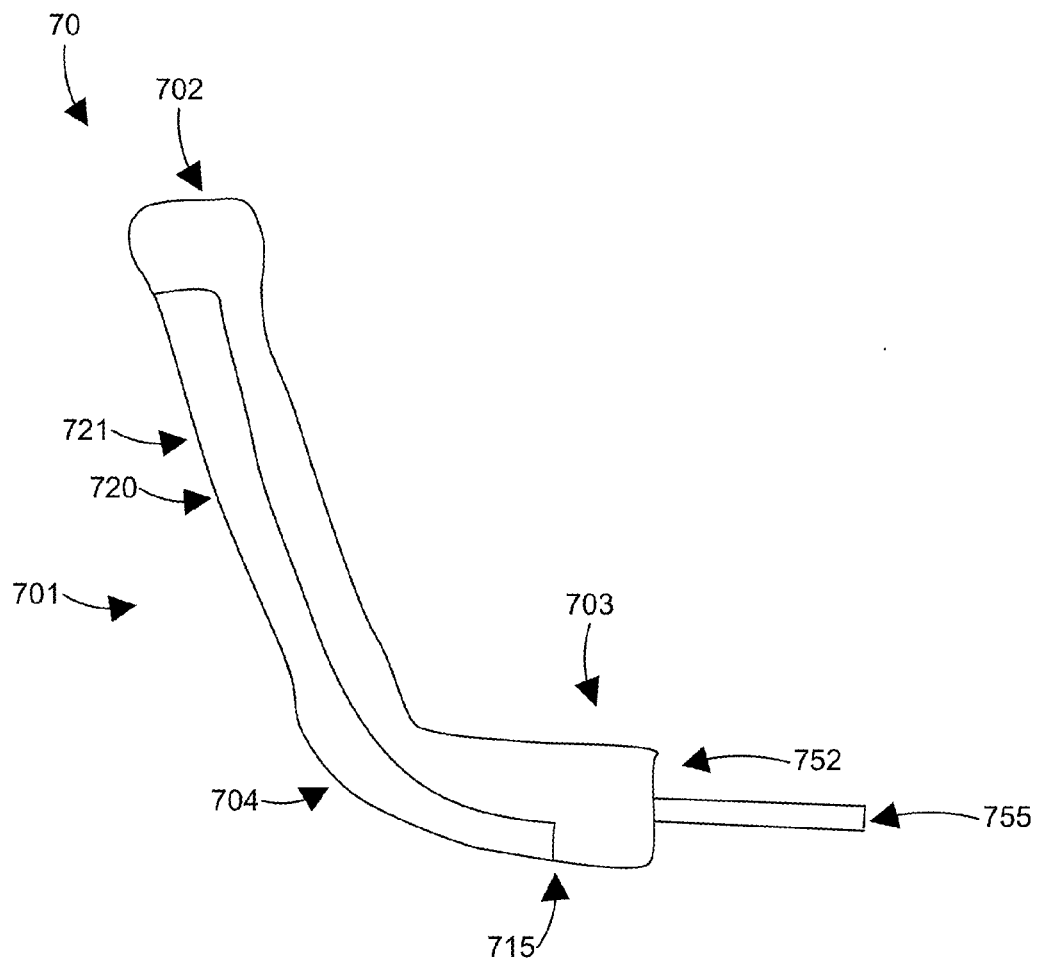
FIG. 7 is a side view of an endocavity thermal control device according to an embodiment.

FIG. 7 is a side view of an endocavity thermal control device 70 according to an embodiment. The device 70 includes an elongated insertable portion 701 and a truncated second portion 703. A bend 704 connects the insertable and second portions 701, 703. In general, the device 70 appears similar to a hockey stick in shape. A cooling window 720 is disposed along a surface 721 of the device 720 from tip 702 to a portion 715 between the bend 704 and the second end 752. A flexible or rigid tube 755 connects to the second end 752 for circulating a thermal fluid in the device 70, as discussed above. In some embodiments, multiple tubes 755 and ports connect to the second end 752 of the device 70. For example, the tubes 755 can include a balloon fill port and tube, a fluid inlet port and tube, a fluid outlet pot and tube, and a purge port and tube. In some embodiments, the purge port can be connected to the inlet tube internally in the second portion 703.

Figure 8:
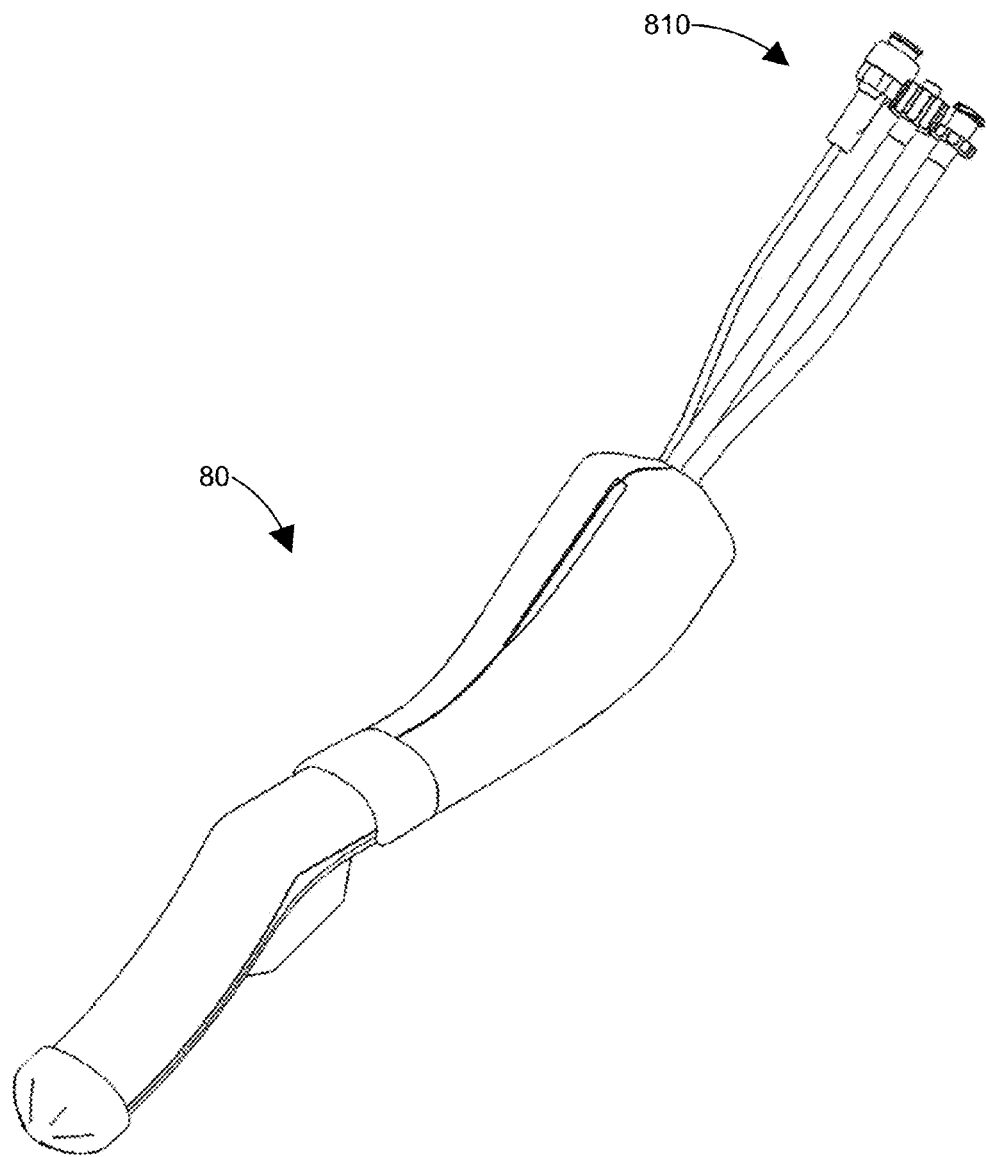
FIG. 8 is a perspective view of an endocavity thermal control device according to an embodiment.
Figure 9:
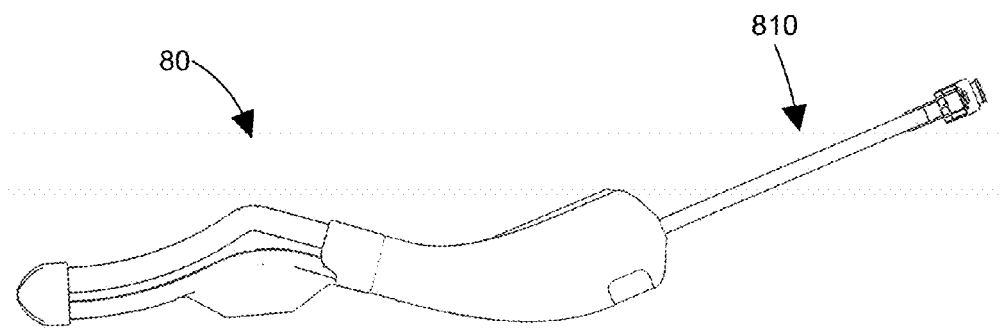
FIG. 9 is a side view of the endocavity thermal control device illustrated in FIG. 8.

FIG. 8 is a perspective view of an endocavity thermal control device 80 according to an embodiment. The device 80 includes a plurality of ports 810 for fluid and electrical connects to the device 80. FIG. 9 is a side view of the device 80 illustrated in FIG. 8.

The present design therefore allows for a safer and more effective cooling device when used in endorectal temperature control (e.g., cooling or heating) applications. In an aspect, the overall shape of the device is angled to generally fit a typical rectal cavity of a patient, including by angling the tip end of the device away from the patient's spine to allow for insertion of the device into the needed position even with a patient having a smaller rectum. In another aspect, the device is contoured to fill an anterior "notch" in the rectum, which is typically caused by or accentuated by the presence of the thermal therapy device in the nearby urethra (e.g., in ultrasound transurethral thermal therapy). In yet another aspect, accounting for and filling in said "notch" brings the cooling device's cooling window closer to the prostate and prostate-rectum interface where cooling is needed the most. In still another aspect, the device's cooling window may be curved or contoured to follow a general contour of the prostate. In another aspect, the device includes an expandable or inflatable element such as a balloon or bladder, on one side thereof, which can controllably increase in volume (be inflated) to cause the device to be pressed more firmly against one side of the endocavity in which it is inserted, e.g., to press the device's cooling window against the rectal wall adjacent to the prostate. Other aspects include a handle with an adjustable collar for securing the device at the proper depth in the patient's endocavity. The handle portion of the device may include control features such as balloon/bladder inflation controls, on/off controls and other actuators and user interface elements. In some aspects the above design avoids unwanted air gaps or bubbles or other gas inclusions from forming or remaining in the device or in the endocavity. Such bubbles or inclusions can adversely affect imaging as well as thermal treatment in the patient because they pose magnetic susceptibility and impedance mismatch interfaces (e.g., gas-liquid or gas-tissue interfaces) which can introduce magnetic susceptibility artifacts in MRI images, reflect ultrasound, laser and RF energy and will scatter or impede the propagation of other therapeutic waves or energy fields in and near the treatment zone.

The above-described device therefore effectively controls the temperature, e.g., by cooling, in and proximal to an endocavity in which it is inserted, e.g., the rectum of a male patient undergoing thermal therapy, e.g., transurethral ultrasound thermal therapy. Those skilled in the art will appreciate the application of the present designs and concepts, including with predictable and equivalent variations adapted to other procedures and cavities in a patient's body as applicable.

The present invention should not be considered limited to the particular embodiments described above, but rather should be understood to cover all aspects of the invention as fairly set out in the present claims. Various modifications, equivalent processes, as well as numerous structures to which the present invention may be applicable, will be readily apparent to those skilled in the art to which the present invention is directed upon review of the present disclosure. The claims are intended to cover such modifications.

What is claimed is:

1. An endocavity thermal control device comprising:
    an elongated body having an insertable portion for insertion into a rectum of a patient and an external portion that remains external to the rectum, wherein the insertable portion includes a distal portion and a proximal portion disposed at a body angle with respect to one another, the body angle being an obtuse angle greater than 90 degrees but less than 180 degrees, the body angle defined by an internal angle of a wall between the distal and proximal portions at an internal bend in the insertable portion;
    a fluid circuit in the elongated body that extends from the external portion to the insertable portion, the fluid circuit configured to circulate a thermal fluid into and out of the insertable portion; and
    a thermal window disposed on a surface of the insertable portion, the thermal window configured to be positioned adjacent to a prostate when the device is inserted into the rectum, the thermal window in thermal communication with the thermal fluid.

2. The device of claim 1, wherein the insertable portion has a curved contour.

3. The device of claim 2, wherein the curved contour is concave such that a tip of the insertable portion is configured to be angled away from a spine of the patient when the device is inserted into the rectum of the patient.

4. The device of claim 1, wherein the elongated body conforms to a shape of a rectal wall adjacent to the prostate when a thermal therapy device is inserted into a urethra of the patient.

5. The device of claim 4, wherein the body angle conforms to a notch formed in the rectal wall, the notch disposed adjacent to an apex of the prostate.

6. The device of claim 5, wherein the body angle conforms to a notch angle formed by the notch.

7. The device of claim 6, wherein the body angle matches the notch angle.

8. The device of claim 7, wherein the body angle and the notch angle are 120 to 140 degrees.

9. The device of claim 8, wherein the body angle and the notch angle are 130 degrees.

10. The device of claim 1, further comprising an inflatable balloon disposed on the elongated body.

11. The device of claim 10, wherein a cross section of the elongated body forms the body angle on a first side of the elongated body and the inflatable balloon is disposed on a second side of the elongated body, the first side opposing the second side.

12. The device of claim 11, wherein the balloon is inflatable up to 30 mm in diameter.

13. The device of claim 11, wherein the balloon is configured to contact a first rectal wall distal to the prostate to cause the second side of the elongated body to contact a second rectal wall proximal to the prostate.

14. The device of claim 1, wherein the thermal window extends at least 20 mm onto the proximal portion of the insertable portion of the elongated body, the proximal portion disposed between the distal portion and the external portion.

15. The device of claim 1, wherein channels are defined in a tip of the insertable portion of the elongated body, the channels extending from the tip towards the insertable portion of the elongated body.

16. The device of claim 1, wherein a cross section of the elongated body has a substantially oval shape.

17. The device of claim 1, wherein the external portion is flared.

18. The device of claim 1, further comprising a fluid purge jet in fluid communication with the thermal window.

19. The device of claim 1, wherein the surface on which the thermal window is disposed includes a concave portion on which a portion of the thermal window is disposed.

20. The device of claim 19, wherein the insertable portion is rigid and the body angle is fixed.

21. A method of controlling a temperature of a prostate during thermal therapy of a patient, the method comprising:
    inserting an endocavity thermal control device into a rectal cavity of the patient, the device comprising an elongated body having an insertable portion and an external portion, wherein the insertable portion includes a distal portion and a proximal portion disposed at a body angle with respect to one another, the body angle being obtuse and greater than 90 degrees but less than 180 degrees, the body angle defined by an internal angle of a wall between the distal and proximal portions at an internal bend in the insertable portion;
    positioning the elongated body to conform to a notch in a rectal wall adjacent to an apex of the prostate, the notch formed when a thermal therapy device is inserted into a urethra of the patient;
    inflating a balloon disposed on the elongated body of the device;
    pressing the balloon against a first rectal wall distal to the prostate to cause a thermal window on the elongated body to contact a second rectal wall proximal to the prostate; and
    circulating a thermal fluid in a fluid circuit in the elongated body, the fluid circuit extending from an external portion to an internal portion of the elongated body, the thermal fluid in thermal communication with the thermal window.

22. The method of claim 21, further comprising adjusting a temperature of the thermal fluid to control the temperature of the prostate.

23. An endocavity thermal control device comprising:
an elongated body having an insertable portion for insertion into a rectum of a patient and an external portion that remains external to the rectum, wherein the insertable portion includes a distal portion and a proximal portion disposed at a body angle with respect to one another, the body angle being an obtuse angle greater than 90 degrees but less than 180 degrees;
a fluid circuit in the body that extends from the external portion to the insertable portion, the fluid circuit configured to circulate a thermal fluid into and out of the insertable portion; and
a thermal window disposed on a concave surface of the insertable portion, the thermal window configured to be positioned adjacent to a prostate when the device is inserted into the rectum, the thermal window in thermal communication with the thermal fluid.

24. The device of claim 23, wherein the concave surface is rigid.

25. The device of claim 23, wherein the insertable portion is rigid and the body angle is fixed.

26. The device of claim 23, wherein the thermal window extends from a bend of the insertable portion that defines the body angle.

27. The device of claim 26, wherein the thermal window extends from the bend of the insertable portion to a front tip of the insertable portion.

28. The device of claim 23, wherein the insertable portion includes a rigid bend that defines the body angle.

29. The device of claim 28, wherein the thermal window includes portions disposed on opposite sides of the rigid bend that defines the body angle.

30. The device of claim 28, wherein the thermal window extends across the rigid bend that defines the body angle.

31. An endocavity thermal control device comprising:
an elongated body having an insertable portion for insertion into a rectum of a patient and an external portion that remains external to the rectum, wherein the insertable portion includes a distal portion and a proximal portion disposed at a body angle with respect to one another, the body angle being an obtuse angle greater than 90 degrees but less than 180 degrees, the body angle defined by a bend in the elongated body that defines a change in axial direction of the elongated body;
a fluid circuit in the body that extends from the external portion to the insertable portion, the fluid circuit configured to circulate a thermal fluid into and out of the insertable portion; and
a thermal window disposed on a surface of the insertable portion, the thermal window configured to be positioned adjacent to a prostate when the device is inserted into the rectum, the thermal window in thermal communication with the thermal fluid.

* * * * *